(12) United States Patent
Mattes et al.

(10) Patent No.: US 9,730,574 B2
(45) Date of Patent: Aug. 15, 2017

(54) ENDOSCOPE

(71) Applicants: Henke-Sass, Wolf GmbH, Tuttlingen (DE); Stryker Corporation, Kalamazoo, MI (US)

(72) Inventors: Andreas Mattes, Duerbheim (DE); Norbert Haeckl, Leibertingen (DE); Stefan Rapp, Villingen-Schwenningen (DE); Thomas Paul Weller, Tuttlingen (DE); Hannah Lawrence, San Jose, CA (US); Candice Pack, Campbell, CA (US)

(73) Assignees: Henke-Sass, Wolf GmbH, Tuttlingen (DE); Stryker Corporation, Kalamazoo, MI (US)

( * ) Notice: Subject to any disclaimer, the term of this patent is extended or adjusted under 35 U.S.C. 154(b) by 229 days.

(21) Appl. No.: 14/516,902

(22) Filed: Oct. 17, 2014

(65) Prior Publication Data
US 2015/0112133 A1 Apr. 23, 2015

(30) Foreign Application Priority Data
Oct. 18, 2013 (DE) .................. 10 2013 221 224

(51) Int. Cl.
*A61B 1/04* (2006.01)
*A61B 1/00* (2006.01)

(52) U.S. Cl.
CPC .......... *A61B 1/042* (2013.01); *A61B 1/00124* (2013.01); *A61B 1/00126* (2013.01); *A61B 1/00163* (2013.01); *A61B 1/00195* (2013.01)

(58) Field of Classification Search
CPC . A61B 1/042; A61B 1/00124; A61B 1/00163; A61B 1/00195; A61B 1/00126; A61B 1/04; G03B 17/48
USPC ........................................................ 600/112
See application file for complete search history.

(56) References Cited

U.S. PATENT DOCUMENTS

| | | | |
|---|---|---|---|
| 5,125,394 A * | 6/1992 | Chatenever | G03B 17/48 600/112 |
| 5,599,278 A * | 2/1997 | Hibbard | A61B 1/00142 600/133 |
| 5,609,561 A | 3/1997 | Uehara et al. | |
| 6,425,857 B1 | 7/2002 | Rudischhauser et al. | |
| 2010/0160734 A1* | 6/2010 | Ivanovic | A61B 1/00096 600/122 |
| 2012/0075639 A1* | 3/2012 | Brennan | A61B 1/00172 356/479 |

FOREIGN PATENT DOCUMENTS

| | | |
|---|---|---|
| EP | 0489240 A1 | 6/1992 |
| WO | 9939623 A1 | 8/1999 |

* cited by examiner

*Primary Examiner* — Timothy J Neal
(74) *Attorney, Agent, or Firm* — Skaar Ulbrich Macari, P.A.

(57) ABSTRACT

An endoscope is provided with an endoscope shaft and a main body connected to the endoscope shaft. The endoscope includes a camera connection to which an optical recording device can be mechanically fixed. The main body is electrically conductive. The camera connection includes an electric insulating body that electrically insulates an optical recording device, mechanically fixed to the camera connection, from the main body.

10 Claims, 2 Drawing Sheets

ENDOSCOPE

PRIORITY

This application claims priority to German Patent Application No. 102013221224.0, filed on Oct. 18, 2013, which is hereby incorporated herein by reference in its entirety.

FIELD

The present invention relates to an endoscope with an endoscope shaft and a main body connected to the endoscope shaft, which main body has a camera connection thereto, which an optical recording device can be mechanically fixed, wherein the main body is electrically conductive.

BACKGROUND

When using an endoscope for optical monitoring in high-frequency surgery, the difficulty can occur, undesirably, that voltage pulses produced are transferred, via the endoscope, all the way to the optical recording device fixed to the endoscope. These voltage pulses can lead to a deterioration in the recording of the image with the image sensor of the optical recording device. In CCD sensors, this can lead to a particularly grainy image. If CMOS sensors are used, even a total image drop-out can occur, in particular because of digital signal processing.

SUMMARY

An object of the invention includes improving an endoscope such that the difficulties discussed above can be overcome as completely as possible. In certain embodiments, this object is achieved with an endoscope comprising a camera connection including an electric insulating body which electrically insulates an optical recording device, mechanically fixed to the camera connection, from the main body. Because of this electrical insulation, the undesired voltage pulses are no longer transferred from the endoscope as far as the optical recording device, with the result that the optical recording device can record the image as desired, uninfluenced by voltage pulses which can occur.

With the endoscope according to certain embodiments of the invention, thus in comparison with known endoscopes, the camera connection is modified such that it includes the electric insulating body. Already existing endoscopes can thus also be converted with the result that, as endoscopes according to the invention, they have the desired electrical insulation between the optical recording device and the remainder of the endoscope.

In particular embodiments, the camera connection can be arranged at the proximal end of the endoscope. Furthermore, the camera connection can be rotated vis-à-vis the main body. In particular, the camera connection can be rotated about a longitudinal axis of the endoscope.

The camera connection can include a metallic ring nut with an external thread onto which a corresponding internal thread of the optical recording device can be screwed. It is thus ensured that there is a good connection between the camera connection and the optical recording device and that this connection can be undone and done up again several times without it leading to a deterioration in the mechanical connection properties.

The metallic ring nut in certain embodiments is preferably arranged on the electric insulating body such that the metallic ring nut is electrically insulated from the main body. In particular, the electric insulating body can have at least one ring which can be rotated vis-à-vis the main body and the ring nut can be connected to the at least one ring in rotation-resistant manner. On the one hand this provides the rotatability of the camera connection and on the other hand ensures the necessary electrical insulation.

The electric insulating body in certain embodiments can be formed from a plastic material. In particular e.g. polyetheretherketone (PEEK) can be used. This plastic is characterised by its high melting point and can be sterilised or autoclaved repeatedly. The electric insulating body can, of course, also be formed from any other suitable dielectric material, or combination of materials. However, it is essential that the material(s) used have the desired electrical insulating property.

The electric insulating body can be formed from one or more parts.

The endoscope according to certain embodiments of the invention can be formed as an optical endoscope which displays an object in front of the endoscope shaft as an image in a focussing plane which lies behind the end of the main body facing away from the endoscope shaft (and thus outside of the main body). For this, imaging optics can be arranged in the endoscope shaft and in the main body. In particular, the imaging optics can be arranged in a hermetically sealed inner space of the endoscope.

The endoscope according to certain embodiments of the invention is capable of being autoclaved. By "capable of being autoclaved" is meant here in particular that, during a predetermined period of time (for example several minutes) the endoscope is subjected to sterilisation by water vapour (in particular saturated water vapour) of at least 100° C. or at least 130° C. without the endoscope being damaged (without in particular water vapour being able to penetrate the endoscope shaft or the inner space of the main body).

The endoscope shaft and the main body are can be formed substantially from a metallic material, such as e.g. stainless steel. Furthermore, the endoscope shaft and the main body are preferably electrically conductive and also connected to one another in an electrically conductive manner.

The endoscope shaft can be formed as a rigid endoscope shaft, as an endoscope shaft with a flexible distal end or as a flexible endoscope shaft.

The endoscope according to certain embodiments of the invention can be formed as a medical endoscope or as a technical endoscope.

The optical recording device can be a digital camera or a digital video camera.

The optical recording device can, but need not, be a component of the endoscope according to certain embodiments of the invention.

It is understood that the features mentioned above and those yet to be explained below can be used not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features essential to the invention.

DETAILED DESCRIPTION

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

Figure 1:
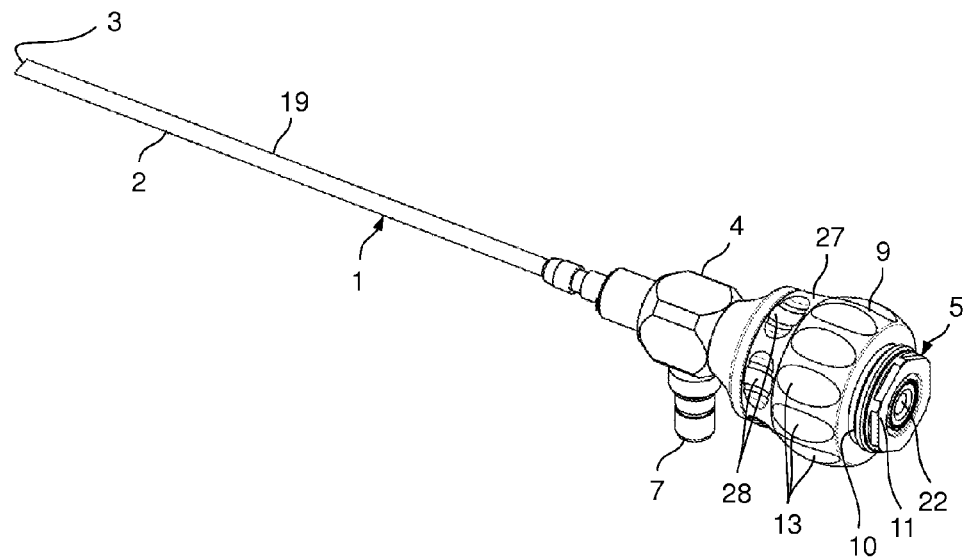
FIG. 1 is a perspective view of an embodiment of the endoscope according to the invention.
Figure 2:
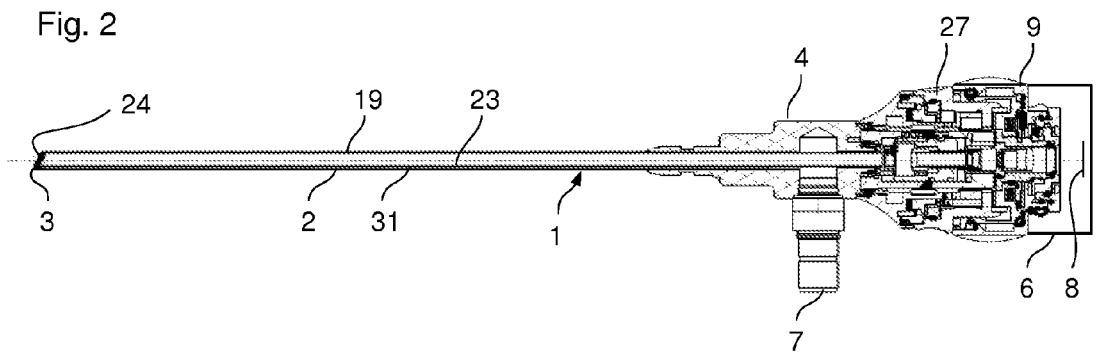
FIG. 2 is a sectional view of the endoscope of FIG. 1.

In the embodiment shown in FIGS. 1 and 2, the endoscope 1 according to the invention comprises an endoscope shaft 2 with a distal end 3 which, at the same time, is also the distal end of the endoscope 1. The end of the endoscope shaft 2 facing away from the distal end 3 is connected to a main body 4 of the endoscope, which main body has a camera connection 5 (e.g. a C-mount connection or a bayonet connection) for an optical recording device 6 (for example a video camera) as well as an illumination connection 7. The optical recording device 6, which for example contains a CMOS sensor 8, is merely drawn in schematically in the representation of FIG. 2 and can, but need not, be part of the endoscope 1 according to the invention.

The endoscope shaft 2 and the main body 4 are, as a rule, predominantly made out of metal (e.g. stainless steel) and are thus electrically conductive.

Figure 3:
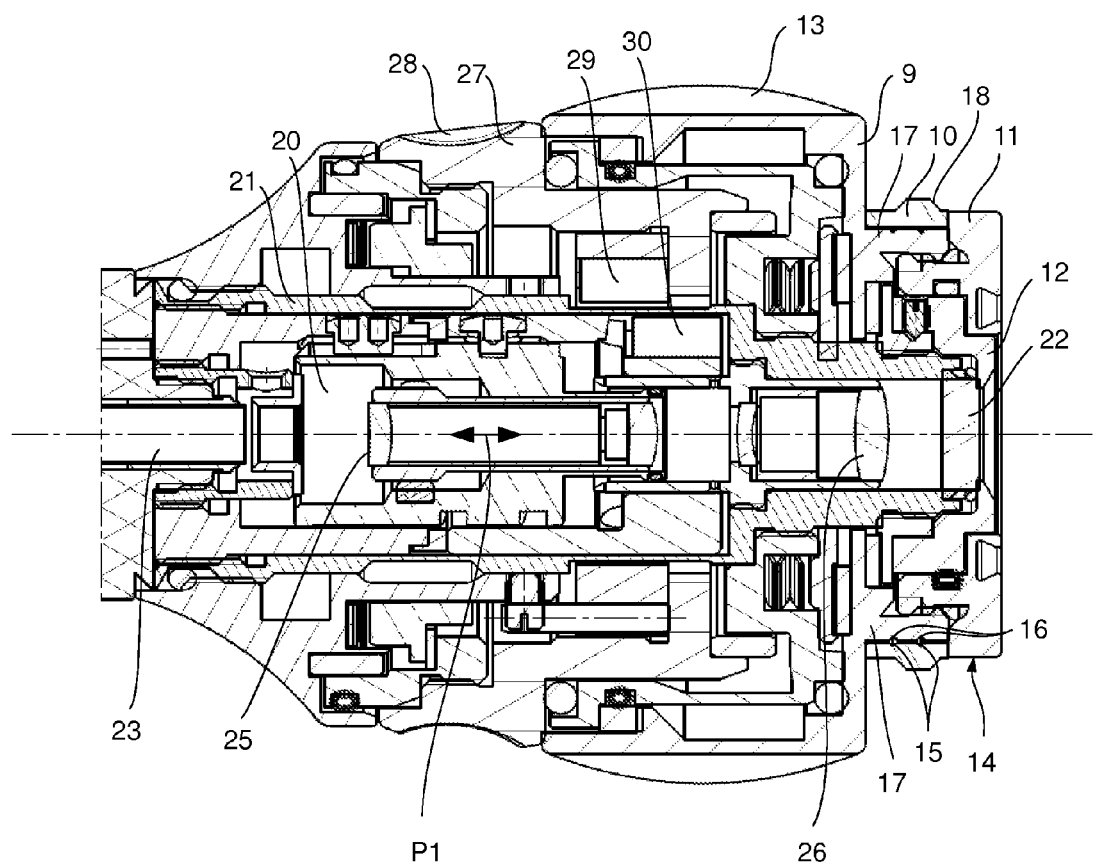
FIG. 3 is an enlarged sectional view of the proximal end region of the main body of the endoscope of FIGS. 1 and 2.

As can be seen in particular in the enlarged sectional representation of FIG. 3, the camera connection 5 comprises a mounting ring 9, a metallic ring nut 10 (or metallic threaded ring 10), a fixing ring 11 and an inner ring 12, wherein the mounting ring 9, the fixing ring 11 and the inner ring 12 are formed from a material which is not electrically conductive, and thus are in particularly formed from an electrically insulating material. A plastic material which can be autoclaved, such as e.g. PEEK (polyetheretherketone), can be used as material.

The mounting ring 9, the ring nut 10 and the fixing ring 11 are connected to one another in rotation-resistant manner and can be rotated together, relative to the remaining parts of the main body 4 as well as relative to the inner ring 12, about the longitudinal axis of the endoscope 1. The ring nut 10 has an external thread 18 onto which a corresponding internal thread of the optical recording device 6 can be screwed. The described rotatability of mounting ring 9, ring nut 10 and fixing ring 11 is provided in order to facilitate this screwing-on, with the result that the optical recording device 6 can be screwed onto the camera connection 5 by rotating these three rings 9 to 11. In order to facilitate this screwing-on, the mounting ring 9 has recessed grips 13 which are arranged alongside one another in peripheral direction.

As the mounting ring 9, the fixing ring 11 and the inner ring 12 are formed from an electrically insulating material, together they form an electric insulating body 14 which sees to it that the optical recording device 6, mechanically connected to the camera connection 5, is electrically insulated from the main body 4. There is no electrical connection between the main body 4 and the optical recording device 6 in the region of the camera connection 5.

The advantage is thus achieved that voltage pulses which can occur e.g. in high-frequency surgery or the use of an electric scalpel and, undesirably, on the endoscope 1 provided for visual monitoring and thus on the endoscope shaft 2, and can be transferred from this to the main body 4, are not transferred to the optical recording device 6 because this is electrically insulated from the main body 4 because of the electric insulating body 14. With CMOS sensors 8, such voltage pulses would lead directly to an undesired image drop-out occurring. This can be prevented effectively in the endoscope 1 according to the invention because of the electric insulating body 14.

The formation of the ring nut 10 as metallic ring nut 10 leads to the advantage that, on the one hand, a good mechanical connection to the optical recording device 6 is possible. On the other hand, repeated screwing-on and off is possible without this leading to a deterioration in the mechanical connection. Since the metallic ring nut 10 is in contact only with the mounting ring 9 and the fixing ring 11, neither of which is electrically conductive, the metallic ring nut 10 is thus likewise insulated from the main body 4 by the electric insulating body 14.

As can be seen from FIG. 3 in particular, the ring nut 10 has on its inside several lugs 15 projecting inwards which are in positive lock with corresponding groove-shaped recesses 16 on the outside of a bearing section 17 of the mounting ring 9, with the result that there is a rotation-resistant connection between the ring nut 10 and the mounting ring 9. The ring nut 10 thus cannot be rotated about the longitudinal axis of the endoscope relative to the mounting ring 9.

The endoscope 1 is designed to be capable of being autoclaved. For this, a hermetically sealed inner space 20 is provided which, as shown in FIG. 3, is bordered by a wall 21 and is hermetically sealed at the proximal end by a proximal cover glass 22 in the proximal end region of the main body 4. The inner space 20 is connected to an inner tube 23 of the endoscope shaft 2 which extends in an outer tube 19 of the endoscope shaft 2 as far as the distal end 3. The inner tube 23 is hermetically sealed with a distal cover glass 24 at the distal end 3 (FIG. 2).

An objective lens (not shown) for recording an image of an object located in front of the distal end 3 is arranged behind the distal cover glass 24 in the inner tube 23. A known optical guide system (e.g. rod lenses or inversion systems which display an input image rotated by 180° at the output end) can be connected to the objective lens, which system transmits the image as far as the proximal end region in the main body 4 in which there is arranged, on the one hand, a group of lenses 25 which can be displaced in longitudinal direction of the endoscope 1 (as indicated by the double-ended arrow P1) and on the other hand a fixed group of lenses 26, which thus cannot be moved in longitudinal direction of the endoscope 1 (both groups of lenses 25, 26 are arranged in the inner space 20). Thus, for example, a focussing on different distances between the image sensors 8 of different optical recording devices 6 is possible. The displaceable group of lenses 25 can be displaced in known manner. Thus, for example, a focussing ring 27 with recessed grips 28 spaced apart from one another in peripheral direction can be provided, which ring has at least one outer magnet 29. Within the inner space 20 at least one inner magnet 30 is provided which is rotatably housed, with the result that a rotation of the focussing ring 27 via the magnetic coupling of the two magnets 29, 30 brings about a rotation of the housing of the inner magnet 30. This rotation is carried out in an axial movement of the displaceable group of lenses 25.

In an alternative embodiment of the endoscope 1 according to the invention no displaceable group of lenses 25 and optionally no fixed group of lenses 26 is provided.

Furthermore, the endoscope, as indicated in FIG. 2, can have a channel 31 between the inner tube 23 and the outer tube 19 of the endoscope shaft 2, which channel extends from the illumination connection 7 as far as the distal end 3 and wherein optical fibres (not shown) are arranged within the channel, which optical fibres are supplied with light via the illumination connection 7, with the result that this light exits at the distal end 3 of the endoscope and can be used to illuminate the object which is to be recorded in front of the distal end 3.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

The invention claimed is:

1. An endoscope, comprising:
    an endoscope shaft; and
    a main body connected to the endoscope shaft, the main body including a camera connection,
    wherein the camera connection is configured to mechanically fix an optical recording device to the main body,
    wherein the main body is electrically conductive,
    wherein the camera connection includes an electric insulating body configured to insulate the optical recording device from the main body when the optical recording device is mechanically fixed to the camera connection, and
    wherein the camera connection includes a metallic ring nut with an external thread onto which a corresponding internal thread of the optical recording device can be screwed.

2. The endoscope according to claim 1, wherein the camera connection is disposed at the proximal end of the endoscope.

3. The endoscope according to claim 2, wherein the electric insulating body includes at least one ring which can be rotated relative to the main body, and the ring nut is connected to the at least one ring in rotation-resistant manner.

4. The endoscope according to claim 1, wherein the camera connection is rotatable relative to the main body.

5. The endoscope according to claim 1, wherein the electric insulating body includes at least one ring which can be rotated relative to the main body, and wherein the ring nut is connected to the at least one ring in a rotation-resistant manner.

6. The endoscope according to claim 1, wherein the electric insulating body is formed of a plastic material.

7. The endoscope according to claim 1, wherein the electric insulating body is formed of polyetheretherketone.

8. The endoscope according to claim 1, wherein imaging optics are disposed in the endoscope shaft and in the main body, the imaging optics configured to display an object in front of the endoscope shaft as an image in a focusing plane which lies behind the end of the main body facing away from the endoscope shaft.

9. The endoscope according to claim 8, wherein the imaging optics are disposed in a hermetically sealed inner space of the endoscope.

10. The endoscope according to claim 1, wherein the endoscope is able to be autoclaved.

* * * * *